Figure 1:
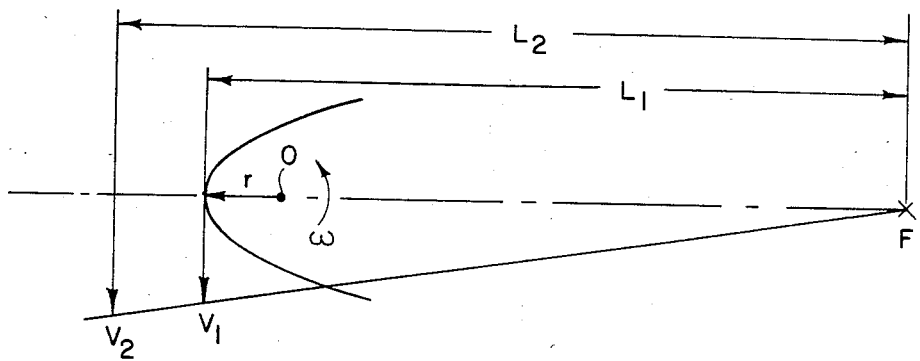

[19] United States Patent
Nieminen

[11] Patent Number: 4,589,122
[45] Date of Patent: May 13, 1986

[54] PANORAMIC TOMOGRAPHY X-RAY APPARATUS

[75] Inventor: Timo Nieminen, Helsinki, Finland

[73] Assignee: Instrumentarium Corp., Finland

[21] Appl. No.: 652,526

[22] Filed: Sep. 20, 1984

[30] Foreign Application Priority Data

Oct. 14, 1983 [FI] Finland ................................ 833754

[51] Int. Cl.$^4$ .............................................. A61B 6/14
[52] U.S. Cl. ........................................ 378/39; 378/40
[58] Field of Search .................................. 378/38–40, 378/21, 168, 191, 197

[56] References Cited

U.S. PATENT DOCUMENTS

| | | | |
|---|---|---|---|
| 3,673,408 | 6/1972 | Moss | 378/39 |
| 4,263,513 | 4/1981 | Palluet | 378/40 |
| 4,264,820 | 4/1981 | Hotta | 378/40 |
| 4,534,048 | 8/1985 | Welander et al. | 378/39 |

Primary Examiner—Craig E. Church
Assistant Examiner—Charles Wieland
Attorney, Agent, or Firm—Andrus, Sceales, Starke & Sawall

[57] ABSTRACT

The invention relates to a panoramic tomography X-ray apparatus, particularly a so-called narrow beam tomographic apparatus for imaging the teeth and jaw area of a patient, wherein an X-ray source (14) and imaging means, e.g. a film cassette (6), are by means of an arm member (13) or the like connected to each other on opposite sides of a target to be imaged and adapted for the actual imaging to be rotated around said target to be imaged. For establishing a constant magnification or enlargement and reducing a radiation dosage the apparatus comprises means for moving said imaging means during the imaging in the direction parallel to a beam of X-rays (15) in a manner that the distance of said imaging means from a selected layer to be imaged remains substantially unchanged. In practice, this is achieved by employing a guide profile (2), from which said imaging means are kept during the imaging at a constant distance by means of a motion in the direction of said beam of X-rays (15).

3 Claims, 3 Drawing Figures

PANORAMIC TOMOGRAPHY X-RAY APPARATUS

The present invention relates to a panoramic tomography X-ray apparatus.

Most of the panoramic devices intended for dental images operate conventionally in a manner that a spinning narrow beam of X-rays passes through a patient's head imaging the dental arch on a suitably moving film flattened in a plane. The question is about tomographic imaging, wherein the film is given such a rate of speed that objects in a desired layer on the jaw arch, e.g. the set of teeth, are imaged sharp while the parts outside said layer are "blurred" out. What is also essential about said methods is that said narrow beam of X-rays is to be directed during the spinning motion so that, at various points, said beam forms a right angle with the jaw arch. The purpose of this is to produce a so-called orthogonal projection in order to prevent a sort of overlapped imaging of the teeth. Another purpose is to achieve imaging of the components of an object or target in proper proportion to each other, i.e. with constant enlargement. For diagnostic reasons it is in practice generally desirable that this constant enlargement be as small as possible.

Due to the configuration of the jaw, the use of prior art equipment leads to a situation where a film cassette, located at a standard distance from an X-ray tube is closer to the patient in the side area than in front. A natural consequence of this is that the enlargement will not be constant but is larger in front than in the side areas.

An object of the invention is to provide a panoramic X-ray apparatus, which is particularly suitable for dental images and in which the prior art drawbacks are eliminated and the above conditions observed as strictly as possible.

Thus, according to the invention, a film is adapted during the imaging not only to run at a suitable rate of speed in the direction orthogonal relative to a projecting beam of rays but also in the direction parallel to said beam of rays. By means of this latter motion, a so-called R-motion, which is radial relative to the spinning motion, it is possible to produce an image practically with a constant enlargement. The practical embodiment is achieved by means of a stationary control profile having the same configuration as the jaw or a like layer to be imaged, a film cassette being kept at a constant distance from said profile by means of said R-motion. For this, a film cassette can be displaced relative to an arm member turning with its mechanism or, alternatively, the entire arm member is displaced in the direction of said beam of X-rays.

By means of the invention, it is possible to bring a film cassette closer to the patient, which in conventional equipment is most of the time required by the spinning motion to be unnecessarily far from a patient. One advantage gained by the invention can also be considered not only the above-mentioned constant enlargement, which in addition is smaller than conventional, but also an X-ray dosage substantially smaller than conventional, this being a direct consequence of a shorter imaging distance and the reduction of required film size.

Figure 3:
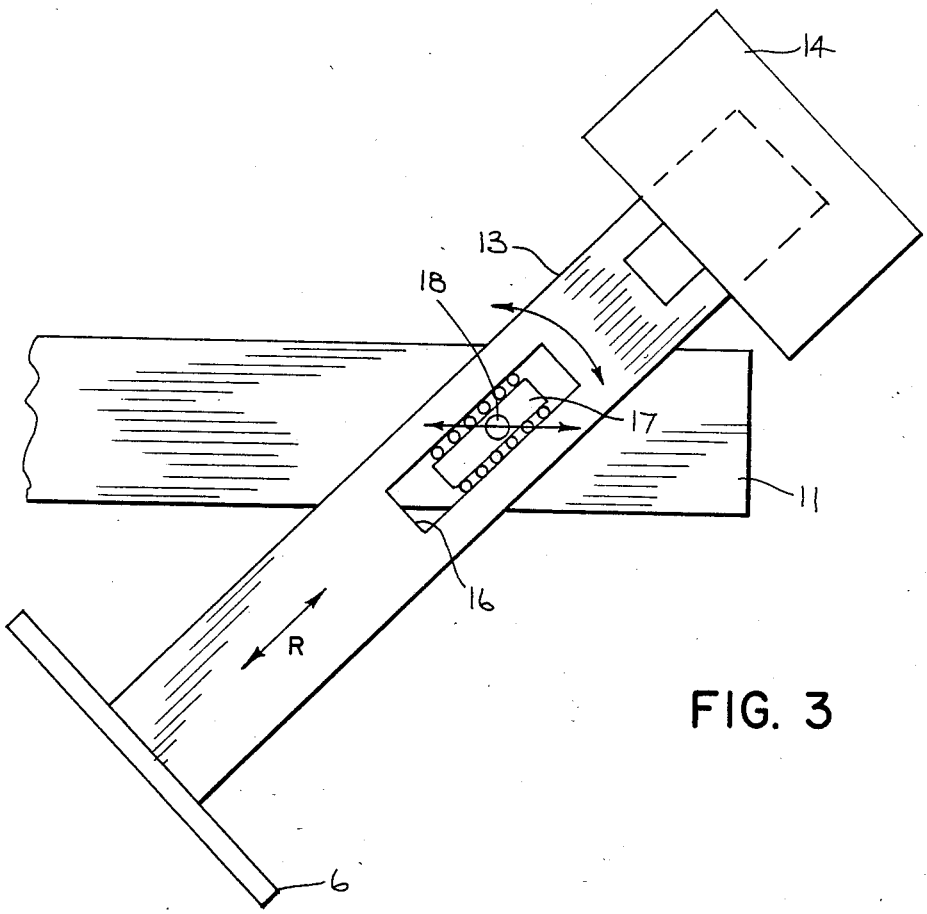
Figure 2:
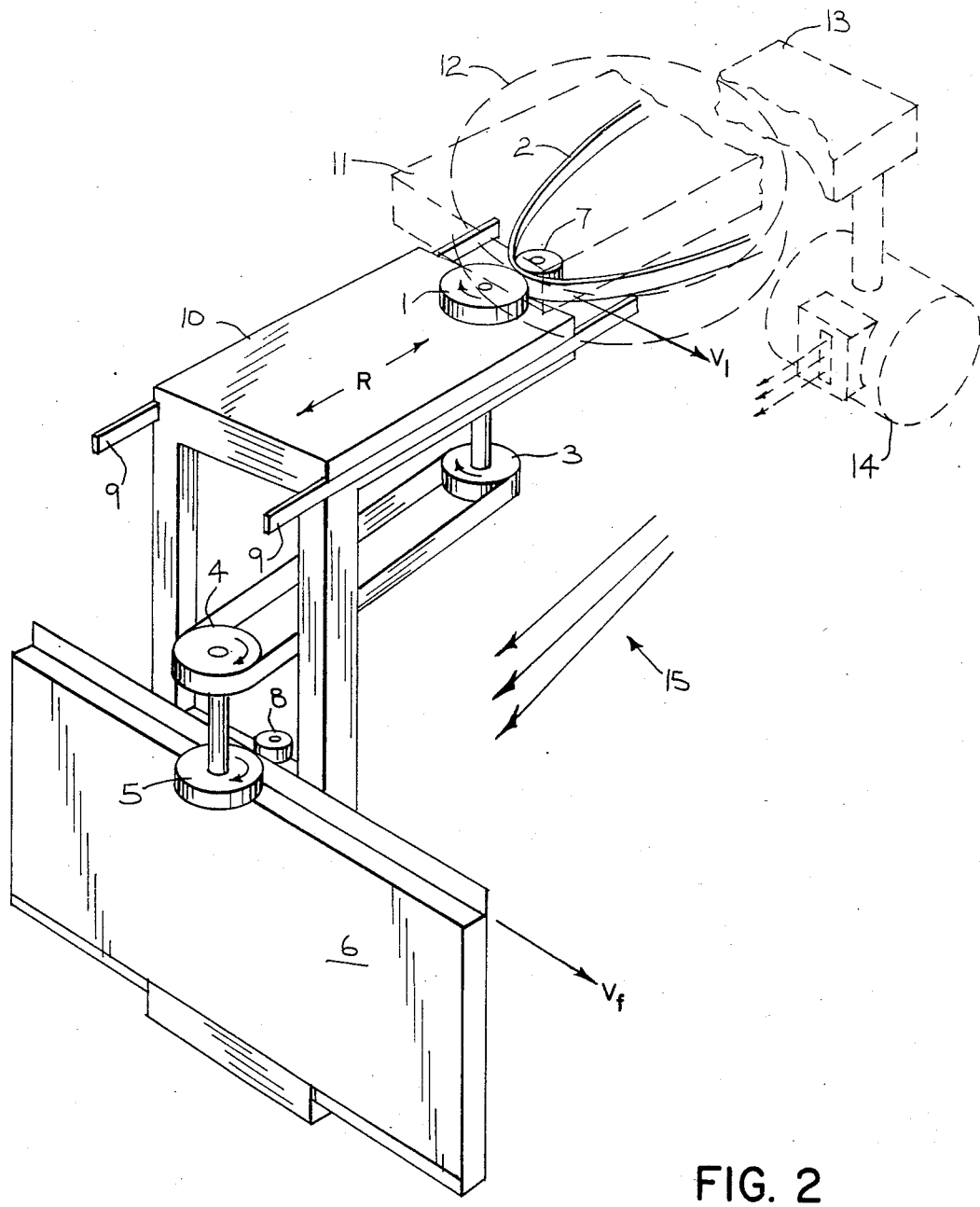

The invention will now be described in more detail with reference made to the accompanying drawing, in which FIG. 1 shows the basic geometry of panoramic techique, FIG. 2 shows one embodiment of the invention in principle, FIG. 3 shows in principle an optional way of effecting the film cassette control motion according to the invention.

Referring to FIG. 1, one basic equation of panoramic imaging can be considered as follows:

$$v_2/v_1 = L_2/L_1, \tag{1}$$

wherein $v_1 = \omega r$.

In the equation:
$L_1$ = distance from focus F to a given spot to be imaged in X-rayed layer
$L_2$ = distance from focus F to film plane
$\omega$ = angular speed around spinning motion center 0
$r$ = distance of a point being imaged from each given center 0 of spinning motion
$v_2$ = speed of an image dot located in image or film plane.

The spinning center of a beam of rays performing the imaging is shifted as the motion progresses in a manner that the orthogonality condition will be fulfilled as well as possible. When determining the speed $v_2$ of an image dot in the image plane, it must be noted that of course focus F functions as projection center.

Equation (1) is a direct consequence of this.

In order to have said image dot appear sharp on the film, the film speed vf must be made by technical means equal to that of the projection of said image dot, i.e. $v_f = v_2$.

Incorporating in equation (1) results $$v_f = (L_2/L_1) \cdot v_1, \tag{2}$$

wherein $L_2/L_1$ is the enlargement of accurate layer i.e. a geometric enlargement. It should be appreciated that, if deviation is made from accurate surface in one direction or another, the enlargement will change especially in horizontal direction substantially due to tomographic reasons.

FIG. 2 discloses one embodiment of the invention suitable for imaging the jaw area and set of teeth, wherein just a film cassette with its mechanism is shifted in R-direction. The mechanism of a film cassette 6 includes a friction wheel 1, journalled to a rotating element 10 and moving along a jaw-shaped, stationary control or guide profile 2. This guide profile 2 is a section of the jaw in a suitable horizontal plane. A result of this is that the peripheral speed of said friction wheel 1 is equal to the speed $v_1$ of the intersection point of a projecting beam of X-rays and the jaw, in other words the surface or layer to be imaged.

Mounted on the same shaft with friction wheel 1 is a pulley 3 for transmitting the spinning motion at gear ratio 1:1 to a pulley 4. Mounted on the same shaft with the latter pulley is another friction wheel 5 which conveys film cassette 6. The ratio of the diameter of friction wheel 5 to that of friction wheel 1 is selected to be the same as the ratio of magnification whereby, according to the above-described basic theory, the object or target projects sharp on the film.

Both friction wheels 1 and 5 are provided with springloaded counterwheels 7 and 8 for reliably squeezing guide profile 2 between the wheels without increasing the friction in the direction of actual spinning motion.

By means of the guide profile shown in FIG. 2, said friction wheel 1 can be made to displace the cassette at a speed multiplied by a desired ratio of magnification. The same guide profile 2 shifts the entire cassette mechanism which, by means of element 10, is also capable of moving on tracks 9 in R-direction. The result will be not only a sharp image but also a constant magnification or enlargement over the entire area.

Dashed lines in FIG. 2 outline other structure of the apparatus, comprising in the first place a fixed frame 11 (just a part of it shown in the figure). Guide profile 2 is by way of an element 12 supportedly mounted on frame 11 so as to make the guide profile immobile at least during the imaging. Mounted on an arm member 13 spinning around the object are an X-ray tube 14 and also guide tracks or rails 9 in order to have said film cassette 6 rotate synchronically with a beam of X-rays 15 around a target to be imaged. Arm member 13 is on one hand rotatably journalled to frame 11 and on the other hand supportedly mounted thereon, so that the center of rotation can be shifted in horizontal plane during the imaging. e.g. in a patient's median sagittal plane, for fulfilling the above orthogonality condition (see FI application No. 763191, corresponding GB Patent No. 1594499).

FIG. 3 illustrates an optional way of performing said R-motion, wherein the entire arm member 13 with its cassette mechanism and X-ray tube is transferred in said direction. In this embodiment, arm member 13 comprises an aperture 16 by means of which said arm member 13, under the control of a control means 17, will be capable of moving in R-direction relative to the rotation axis 18 and frame 11. In other respects, the guide profile arrangement itself matches that shown in FIG. 2 but naturally there is no need for guide rails 9 since the element 10 shown in FIG. 2 is in the case shown in FIG. 3 a fixed part of arm member 13.

A difference between the illustrated embodiments is mainly that, in the case of FIG. 3, a constant magnification is slightly smaller than in the case of FIG. 2.

The invention is by no means limited to the above embodiments but a plurality of modifications thereof are conceivable within the scope of the annexed claims.

I claim:

1. A beam panoramic tomography X-ray apparatus, for imaging the teeth and jaw area of a patient, wherein an X-ray source (14) and an image recording layer (6), are by means of an arm member (13) connected to each other on opposite sides of said area to be imaged for rotation around said area to be imaged, said apparatus comprising means (1, 2, 7, 9, 10) for moving said image recording layer during the imaging in the direction parallel to a beam of X-rays (15) in a manner such that the distance of said image recording layer from a layer to be imaged remains substantially unchanged, as well as means (1–5) for shifting said image recording layer during the imaging in the direction perpendicular to said beam of X-rays (15) at a rate of speed which, by the ratio of magnification, exceeds the rate of speed of the intersection between a projecting beam of X-rays (15) and a surface or layer to be imaged, characterized in that said apparatus comprises a guide profile (2), having the same configuration as a layer to be imaged and being stationary relative to a patient during the imaging, and an image recording layer (6) shifting mechanism (1 . . . 5, 7 . . . 10) having means for following said guide profile (2) during imaging, the movement of said image recording layer (6) in the direction of said beam of X-rays (15) being achieved by moving said image recording layer in a manner such that the distance between the image recording layer (6) and X-ray source (14) changes.

2. An X-ray apparatus as set forth in claim 1, characterized in that said following of guide profile (2) is acheived by means of a friction wheel (1) and that the motion of said friction wheel (1) is further transmitted for the shifting motion of said image recording layer (6) orthogonally relative to the beam of X-rays (15).

3. An X-ray apparatus as set forth in claim 1 or 2, characterized in that for the motion of image recording layer (6) in the direction parallel to said beam of X-rays (15) said image recording layer (6) is mounted on said arm member (13) connecting said image recording layer and X-ray source (14), so that said image recording layer is movable in the direction of said motion.

* * * * *